United States Patent
Pierre

(10) Patent No.: US 10,182,977 B2
(45) Date of Patent: Jan. 22, 2019

(54) HYALURONIC ACID FORMULATION CONTAINING PYRUVATE

(71) Applicant: Allergan Industrie S.A.S., Pringy (FR)

(72) Inventor: Sebastien Pierre, Annecy (FR)

(73) Assignee: Allergan Industrie, S.A.S., Pringy (FR)

( * ) Notice: Subject to any disclaimer, the term of this patent is extended or adjusted under 35 U.S.C. 154(b) by 0 days.

(21) Appl. No.: 15/228,901

(22) Filed: Aug. 4, 2016

(65) Prior Publication Data

US 2016/0338925 A1 Nov. 24, 2016

Related U.S. Application Data

(63) Continuation of application No. 14/414,672, filed as application No. PCT/IB2012/001525 on Jul. 18, 2012, now abandoned.

(51) Int. Cl.

| | |
|---|---|
| *A61K 8/36* | (2006.01) |
| *A61K 8/02* | (2006.01) |
| *A61K 8/55* | (2006.01) |
| *A61K 8/73* | (2006.01) |
| *A61K 8/42* | (2006.01) |
| *A61K 8/365* | (2006.01) |
| *A61L 27/52* | (2006.01) |
| *A61L 27/54* | (2006.01) |
| *A61L 27/50* | (2006.01) |
| *A61Q 19/08* | (2006.01) |
| *A61K 8/04* | (2006.01) |
| *A61L 27/20* | (2006.01) |
| *A61K 8/67* | (2006.01) |

(52) U.S. Cl.
CPC .............. *A61K 8/36* (2013.01); *A61K 8/0216* (2013.01); *A61K 8/042* (2013.01); *A61K 8/365* (2013.01); *A61K 8/42* (2013.01); *A61K 8/55* (2013.01); *A61K 8/676* (2013.01); *A61K 8/73* (2013.01); *A61K 8/735* (2013.01); *A61L 27/20* (2013.01); *A61L 27/505* (2013.01); *A61L 27/52* (2013.01); *A61L 27/54* (2013.01); *A61Q 19/08* (2013.01); *A61K 2800/52* (2013.01); *A61K 2800/591* (2013.01); *A61K 2800/91* (2013.01); *A61L 2300/402* (2013.01); *A61L 2300/428* (2013.01); *A61L 2430/34* (2013.01)

(58) Field of Classification Search
CPC .......... A61K 8/36; A61K 8/365; A61K 8/735; A61K 8/042; A61K 8/42; A61K 8/55; A61K 8/73; A61K 8/0216; A61L 27/20; A61L 27/505; A61L 27/52; A61L 27/54; A61Q 19/08
See application file for complete search history.

(56) References Cited

U.S. PATENT DOCUMENTS

| | | | | |
|---|---|---|---|---|
| 4,521,375 | A | * | 6/1985 | Houlsby .............. A01N 59/00 134/27 |
| 2003/0068297 | A1 | | 4/2003 | Jain |
| 2010/0028437 | A1 | | 2/2010 | Lebreton |
| 2011/0171311 | A1 | | 7/2011 | Gousse et al. |
| 2012/0121534 | A1 | | 5/2012 | Thorel et al. |

FOREIGN PATENT DOCUMENTS

| | | |
|---|---|---|
| CN | 101423559 A | 5/2009 |
| GB | 2344996 A | 6/2000 |
| KR | 20080024426 A | 3/2008 |
| WO | 2012062775 A1 | 5/2012 |

OTHER PUBLICATIONS

Stern et al., Biotechnology Advances, 2007, 25, p. 537-557. (Year: 2007).*
Milas et al., Biopolymers, 2001, 59, p. 191-204. (Year: 2001).*
Kalo Cell Line Anti-Cellulite Cream, Database Accession No. 75211, Oct. 2000, 2 Pages.

* cited by examiner

*Primary Examiner* — Jonathan S Lau
(74) *Attorney, Agent, or Firm* — Nathan S. Smith; Morgan, Lewis & Bockius LLP

(57) ABSTRACT

Pyruvate may be used to stabilize hyaluronic acid compositions. For example, these compositions may have improved heat and/or storage stability.

19 Claims, 4 Drawing Sheets

HYALURONIC ACID FORMULATION CONTAINING PYRUVATE

CROSS REFERENCE TO RELATED APPLICATIONS

This application is a continuation of U.S. application Ser. No. 14/414,672, filed Jan. 13, 2015, which is a U.S. National Phase application under 35 U.S.C. § 371 of PCT Application Serial No. PCT/IB2012/001525 filed Jul. 18, 2012, the entire disclosure of each of these applications being incorporated herein by reference in its entirety.

BACKGROUND

Skin aging is a progressive phenomenon, occurs over time and can be affected by lifestyle factors, such as alcohol consumption, tobacco use and sun exposure. Aging of the facial skin can be characterized by atrophy, slackening, and fattening. Atrophy corresponds to a massive reduction of the thickness of skin tissue. Slackening of the subcutaneous tissues may lead to an excess of skin and ptosis can and lead to the appearance of drooping cheeks and eye lids. Fattening refers to an increase in excess weight by swelling of the bottom of the face and neck. These changes are typically associated with dryness, loss of elasticity, and rough texture.

Hyaluronan, also known as hyaluronic acid (HA) is distributed widely throughout the human body in connective and epithelial tissues and abundant in the different layers of the skin, where it has multiple functions such as, e.g., to ensure good hydration, to assist in the organization of the extracellular matrix, to act as a filler material, and to participate in tissue repair mechanisms. However, with age, the quantity of HA, collagen, elastin, and other matrix polymers present in the skin decreases. For example, repeated exposed to ultra violet light, e.g., from the sun, causes dermal cells to both decrease their production of HA as well as increase the rate of their degradation. This HA loss can result in various skin conditions such as, e.g., imperfects, defects, diseases and/or disorders, and the like. For instance, there is a strong correlation between the water content in the skin and levels of HA in the dermal tissue. As skin ages, the amount and quality of HA in the skin is reduced. These changes lead to drying and wrinkling of the skin.

Dermal fillers are useful in treating soft tissue conditions and in other skin therapies because the fillers can replace lost endogenous matrix polymers, or enhance/facilitate the function of existing matrix polymers, in order to treat these skin conditions. In the past, such compositions have been used in cosmetic applications to fill wrinkles, lines, folds, scars, and to enhance dermal tissue, such as, e.g., to plump thin lips, or fill-in sunken eyes or shallow cheeks. One common matrix polymer used in dermal filler compositions is HA. Because HA is natural to the human body, it is a generally well tolerated and a fairly low risk treatment for a wide variety of skin conditions. Unfortunately, some HA compositions are less stable to sterilization, such as heat sterilization, than may be desired.

SUMMARY

When incorporated into a hyaluronic acid composition, pyruvate may help to stabilize hyaluronic acid and/or other additives that might be present in the composition.

Some embodiments include a composition comprising: a hyaluronic acid and pyruvate, wherein the hyaluronic acid is crosslinked, the composition is suitable for use as a dermal filler, and the composition is a gel that is stable to heat sterilization.

Some embodiments include a composition prepared by a process comprising: heat treating a gel comprising a crosslinked hyaluronic acid and a pyruvate.

Some embodiments include a dermal filler product comprising a composition described herein.

Some embodiments include a method of improving the thermal stability of a dermal filler product, comprising: forming a gel comprising a combination of pyruvate and a crosslinked hyaluronic acid; wherein the pyruvate is effective to improve the thermal stability of the gel.

DETAILED DESCRIPTION

Figure 1:
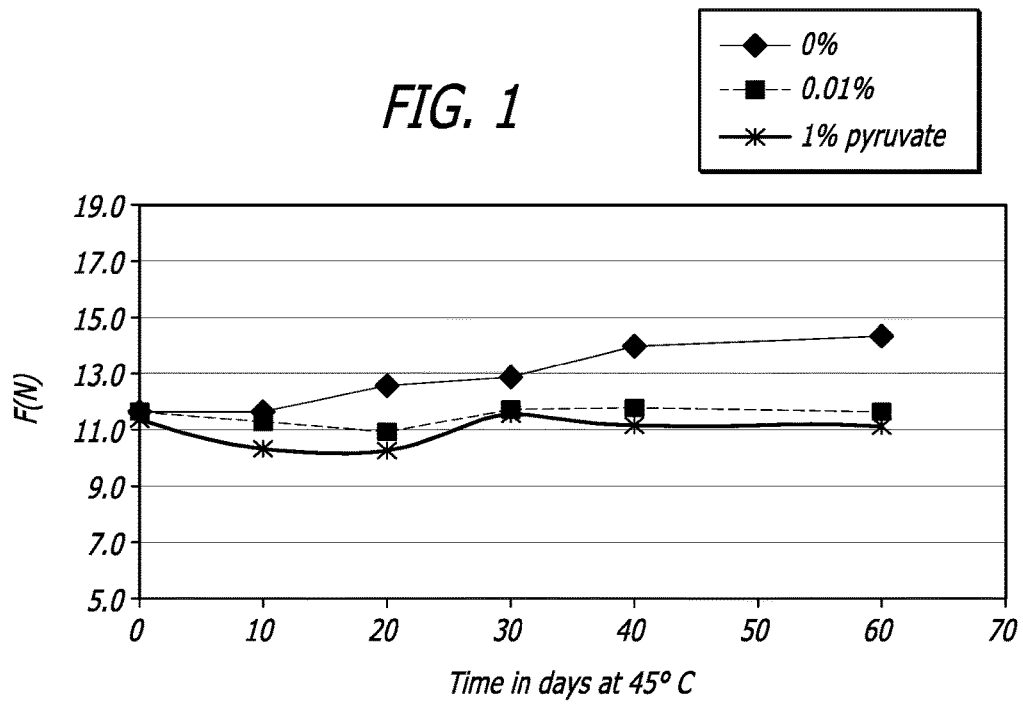
FIG. 1 is a plot of extrusion force of some compositions of Example 1 as they are stored at 45° C. for 60 days.

A pyruvate, such as, sodium pyruvate may be added to a hyaluronic acid composition to help stabilize the composition. For example, the addition of sodium pyruvate or another pyruvate, may have a significant impact on the stability of a hyaluronic acid gel (e.g. sterilization and thermal stability) and the other ingredients present in the formulation (such as sodium ascorbyl phosphate or vitagen).

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups. Unless clearly indicated otherwise, reference to hyaluronic acid, hyaluronan, or HA herein may include its fully protonated, or nonionic form as depicted below, as well as any anionic forms and salts of hyaluronic acid, such as sodium salts, potassium salts, lithium salts, magnesium salts, calcium salts, etc.

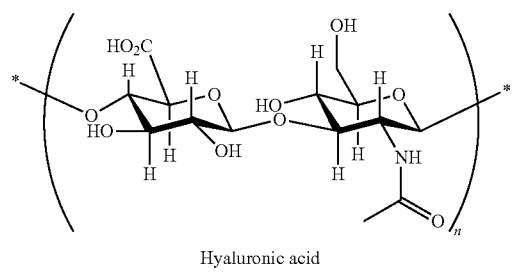

Hyaluronic acid

Any suitable amount of HA may be used in a composition, such as about 0.1% w/w to about 5% w/w; about 0.5% w/w to about 3% w/w; about 1% w/w to about 2.5% w/w; about 1% w/w to about 2% w/w; about 2% w/w to about 3% w/w; about 0.5% w/w; about 0.6%; about 1.2% w/w; about 1.25% w/w; about 1.3% w/w; about 1.35% w/w; about 1.4% w/w; about 1.5% w/w; about 1.75% w/w; about 2% w/w; about 2.4% w/w; about 2.5% w/w; or any concentration in a range bounded by, or between, any of these values.

An HA may have any suitable molecular weight, such as an average molecular weight of about 5,000 Da to about 20,000,000 Da; about 300,000 Da to about 800,000 Da; or about 2,000,000 Da to about 5,000,000 Da.

In some embodiments, an HA comprises both high molecular weight HA and low molecular weight HA, wherein the high molecular weight HA has a molecular weight greater than about 2,000,000 Da and wherein the low molecular weight HA has a molecular weight of less than about 1,000,000 Da.

In some compositions, an HA may have a low molecular weight, e.g., about 100,000 Da, about 200,000 Da, about 300,000 Da, about 400,000 Da, about 500,000 Da, about 600,000 Da, about 700,000 Da, about 800,000 Da, about 900,000 Da, at most about 100,000 Da, at most about 200,000 Da, at most about 300,000 Da, at most about 400,000 Da, at most about 500,000 Da, at most about 600,000 Da, at most about 700,000 Da, at most about 800,000 Da, at most about 900,000 Da, at most about 950,000 Da, about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In some embodiments, an HA may have a high molecular weight, such as about 1,000,000 Da, about 1,500,000 Da, about 2,000,000 Da, about 2,500,000 Da, about 3,000,000 Da, about 3,500,000 Da, about 4,000,000 Da, about 4,500,000 Da, about 5,000,000 Da, at least about 1,000,000 Da, at least about 1,500,000 Da, at least about 2,000,000 Da, at least about 2,500,000 Da, at least about 3,000,000 Da, at least about 3,500,000 Da, at least about 4,000,000 Da, at least about 4,500,000 Da, or at least about 5,000,000 Da, about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da.

An HA may be a combination of a low molecular weight HA fraction and a high molecular weight HA fraction. A high molecular weight HA fraction includes HA having a mean molecular weight of about 1,000,000 Da or greater, such as about 1,500,000 Da, about 2,000,000 Da, about 2,500,000 Da, about 3,000,000 Da, about 3,500,000 Da, about 4,000,000 Da, about 4,500,000 Da, or about 5,000,000 Da. A low molecular weight HA fraction includes HA having a mean molecular weight of less than about 1,000,000 Da, such as about 200,000 Da, about 300,000 Da, about 400,000 Da, about 500,000 Da, about 600,000 Da, about 700,000 Da, of about 800,000 Da, or about 900,000 Da.

In an HA composition comprising a low molecular weight HA fraction and a high molecular weight HA fraction, any suitable ratio of high molecular weight HA to low molecular weight HA may be used. In some embodiments the weight ratio of high molecular weight HA to low molecular weight HA may be about 20, about 15, about 10, about 5, about 1, about 0.07, about 0.05, about 0.2, or about 0.1. A weight ratio is the quotient (weight high molecular weight HA)/(low molecular weight HA). For example a composition having 20 g of high molecular weight HA and 1 g low molecular weight HA has a weight ratio of high molecular weight HA to low molecular weight HA of 20.

An uncrosslinked HA fraction may also improve the rheological properties of an HA composition so as to improve treatment of a skin condition. In aspects of this embodiment, a composition comprises an uncrosslinked HA where the uncrosslinked HA is present at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, about 20 mg/g, about 40 mg/g, at least about 1 mg/g, at least about 2 mg/g, at least about 3 mg/g, at least about 4 mg/g, at least about 5 mg/g, at least about 10 mg/g, at least about 15 mg/g, at least about 20 mg/g, at least about 25 mg/g, at least about 35 mg/g, at most about 1 mg/g, at most about 2 mg/g, at most about 3 mg/g, at most about 4 mg/g, at most about 5 mg/g, at most about 10 mg/g, at most about 15 mg/g, at most about 20 mg/g, at most about 25 mg/g, about 1 mg/g to about 40 mg/g, about 7.5 mg/g to about 19.5 mg/g, about 8.8 mg/g to about 19 mg/g, about 9 mg/g to about 18 mg/g, about 10 mg/g to about 17 mg/g, about 11 mg/g to about 16 mg/g, or about 12 mg/g to about 15 mg/g. In some embodiments, the ratio of crosslinked HA to uncrosslinked HA is about 0.001 to about 100, about 0.005 to about 20, or about 0.01 to about 0.05.

An HA may be crosslinked, partially crosslinked, or substantially uncrosslinked. In some embodiments, a low molecular weight HA fraction may be crosslinked, a low molecular weight HA fraction may be partially crosslinked, or a low molecular weight HA fraction may be uncrosslinked; and a high molecular weight HA fraction may be crosslinked, a high molecular weight fraction may be partially crosslinked, or a high molecular weight HA fraction may be uncrosslinked.

A crosslinked HA may result from linking two or more individual HA molecules, either directly or by a linking moiety. Crosslinking HA may increase the viscosity of an aqueous HA composition, which may result in the formation of a hydrogel. HA may be crosslinked using dialdehyde or disulfide crosslinking agents including, without limitation, multifunctional PEG-based crosslinking agents, divinyl sulfones, diglycidyl ethers, bis-epoxides, and biscarbodiimides. Non-limiting examples of crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide).), adipic dihydrazide (ADH), bis (sulfosuccinimidyl)suberate (BS), hexamethylenediamine (NMDA), 1-(2,3-epoxypropyl)-2,3-epoxycyclohexane, or combinations thereof. Other useful cross-linking agents are disclosed in Stroumpoulis and Tezel, Tunably Crosslinked Polysaccharide Compositions, US2011/0077737, which is incorporated by reference in its entirety. Non-limiting methods of crosslinking HA are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

The term "pyruvate" generally includes pyruvic acid and/or salts of pyruvic acid such as sodium salts, potassium salts, lithium salts, magnesium salts, calcium salts, etc. Pyruvate may help to stabilize an HA composition. For example pyruvate may stabilize HA and/or other components in an HA composition, such as lidocaine, ascorbic acid, sodium ascorbyl phosphate, vitagen, etc.

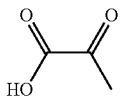

Pyruvic Acid

Any suitable amount of pyruvate may be used, such as about 0.05% w/w to about 2% w/w; about 0.05% w/w to about 1% w/w; about 0.1% w/w to about 1% w/w; about 0.01% w/w to about 2% w/w; about 0.01% w/w, about 0.05% w/w, about 0.1% w/w, about 0.25% w/w, about 0.5% w/w, about 1% w/w, or any amount in a range bounded by, or between, any of these values.

An HA composition may optionally comprise an anesthetic agent. An anesthetic agent may be a local anesthetic agent, including an anesthetic agent that causes a reversible local anesthesia or a loss of nociception, such as, e.g., aminoamide local anesthetics and aminoester local anesthetics. Non-limiting examples of anesthetic agents may include lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, trimecaine, or a combination thereof.

The amount of an anesthetic agent included may be an amount effective to reduce pain experienced by an individual upon administration of the composition, such as about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, about 10%, at least about 0.1%, at least about 0.2%, at least about 0.3%, at least about 0.4%, at least about 0.5%, at least about 0.6%, at least about 0.7%, at least about 0.8% at least about 0.9%, at least about 1.0%, at least about 2.0%, at least about 3.0%, at least about 4.0%, at least about 5.0%, at least about 6.0%, at least about 7.0%, at least about 8.0%, at least about 9.0%, at least about 10%, at most about 0.1%, at most about 0.2%, at most about 0.3%, at most about 0.4%, at most about 0.5%, at most about 0.6%, at most about 0.7%, at most about 0.8% at most about 0.9%, at most about 1.0%, at most about 2.0%, at most about 3.0%, at most about 4.0%, at most about 5.0%, at most about 6.0%, at most about 7.0%, at most about 8.0%, at most about 9.0%, at most about 10%, about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0%.

Some HA compositions may comprise lidocaine, in free base or salt form (e.g. lidocaine HCl) in an amount of about 0.05% w/w to about 1% w/w; about 0.1% w/w to about 0.5% w/w, or about 0.3% w/w.

Some HA compositions do not have an anesthetic agent.

Vitagen (3-aminopropyl-L-ascorbylphosphate), a protected form of vitamin C (ascorbic acid), may be included in an HA composition as an anti-oxidant. Any suitable amount of vitagen may be used, such as about 0.01% w/w to about 2% w/w, about 0.1% w/w to about 1% w/w, about 0.5% w/w to about 0.7% w/w, or about 0.6% w/w.

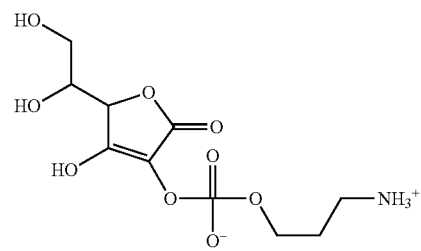

Some compositions may have a physiologically-acceptable osmolarity, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, about 500 mOsm/L, at least about 100 mOsm/L, at least about 150 mOsm/L, at least about 200 mOsm/L, at least about 250 mOsm/L, at most about 300 mOsm/L, at most about 350 mOsm/L, at most about 400 mOsm/L, at most about 450 mOsm/L, at most about 500 mOsm/L, about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L. Osmolality agents may be used to adjust osmolality. Examples include, but are not limited to, salts such as, e.g., sodium chloride and potassium chloride; and glycerin.

Some HA compositions may be suitable for use as a dermal filler. For example, such an HA composition may be in the proper form, e.g. as a gel having an appropriate elastic modulus and viscous modulus, so as to be suitable as a dermal filler. By contrast, an HA composition that is too hard or stiff, or too liquid, may not be suitable for use as a dermal filler. Additionally, a dermal filler may have a composition that is compatible with the part of the body into which it is injected.

An HA composition may be injectable, or capable of being administered into a skin region of an individual by injection through a fine needle, such as a needle that is about 27 gauge or smaller. In some embodiments, an HA composition is injectable through a needle of, e.g., about 27 gauge; about 30 gauge; about 32 gauge; about 22 gauge or smaller; about 27 gauge or smaller; about 30 gauge or smaller; about 32 gauge or smaller; about 22 gauge to about 35 gauge; about 22 gauge to about 34 gauge; about 22 gauge to about 33 gauge; about 22 gauge to about 32 gauge; about 22 gauge to about 27 gauge; or about 27 gauge to about 32 gauge.

An HA composition disclosed may optionally include, without limitation, other pharmaceutically acceptable components, including, without limitation, buffers, preservatives, tonicity adjusters, salts, antioxidants, osmolality adjusting agents, emulsifying agents, wetting agents, sweetening or flavoring agents, and the like.

Non-limiting examples of buffers include acetate buffers, borate buffers, citrate buffers, neutral buffered salines, phosphate buffers, and phosphate buffered salines. Any concentration of a buffer can be used, such as about 0.1 mM to about 900 mM. In some embodiments, an HA composition may have a pH of about 5.0 to about 8.5, about 5.0 to about 8.0, about 6.5 to about 7.5, about 7.0 to about 7.4, or about 7.1 to about 7.3.

Preservatives include, without limitation, sodium metabisulfite, sodium thiosulfate, acetylcysteine, butylated hydroxyanisole, butylated hydroxytoluene, benzalkonium chloride, chlorobutanol, thimerosal, phenylmercuric acetate, phenylmercuric nitrate, a stabilized oxy chloro composition, such as, e.g., PURITE® (Allergan, Inc. Irvine, Calif.) and chelants, such as, e.g., DTPA or DTPA-bisamide, calcium DTPA, and CaNaDTPA-bisamide.

An HA composition may be substantially stable at room temperature, e.g., for about 3 months, about 6 months, about 9 months, about 12 months, about 15 months, about 18 months, about 21 months, about 24 months, about 27 months, about 30 months, about 33 months, about 36 months, at least about 3 months, at least about 6 months, at least about 9 months, at least about 12 months, at least about 15 months, at least about 18 months, at least about 21 months, at least about 24 months, at least about 27 months, at least about 30 months, at least about 33 months, at least about 36 months, about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

The elastic modulus of an object includes the slope of its stress-strain curve in the elastic deformation region: $\lambda$=stress/strain, where $\lambda$ is the elastic modulus in Pascal's (Pa); stress is the force causing the deformation divided by the area to which the force is applied; and strain is the ratio of the change caused by the stress to the original state of the object. Although depending on the speed at which the force is applied, a stiffer composition will have a higher elastic modulus and it will take a greater force to deform the material a given distance, such as, e.g., an injection. Specifying how stresses are to be measured, including directions, may allow many types of elastic moduli to be defined.

Viscous modulus is also known as the loss modulus because it describes the energy that is lost as viscous dissipation. Tan $\delta$ is the ratio of the viscous modulus and the elastic modulus, Tan $\delta$=G"/G'. For Tan $\delta$ values disclosed in the present specification, a Tan $\delta$ is obtained from the dynamic modulus at a frequency of 1 Hz. A lower tan $\delta$ corresponds to a stiffer, harder, or more elastic composition.

In some embodiments, an HA composition can be injected through a 27 gauge needle at a speed of about 13 mm/min with an extrusion force of about 9 N to about 13 N, about 10 N to about 12 N, or about 11 N.

Some HA composition comprising pyruvate may have improved stability to heat, such as heat sterilization, or during storage.

In some embodiments, an HA composition may be heat sterilized at least about 100° C., and remain substantially stable at room temperature for at least about 12 months after heat sterilization.

Some embodiments include method of preparing a hydrogel composition comprising heat treating a mixture of hyaluronic acid and pyruvate. A hydrogel thus treated may maintain the desired hydrogel properties disclosed herein.

In some embodiments, an HA gel has improved thermal stability as compared to a substantially identical gel lacking pyruvate. One method for assessing heat stability is by obtaining a $\Delta$ Tan $\delta$ 1 Hz, which is the difference between the Tan $\delta$ 1 Hz with additives and without additives as shown in the formula below:

$$\Delta \text{ Tan } \delta 1 \text{ Hz} = (\text{Tan } \delta 1 \text{ Hz gel with additives}) - (\text{Tan } \delta 1 \text{ Hz NaHA control})$$

A gel is considered as stable if $\Delta$ Tan $\delta$ 1 Hz$\leq$0.1 in conjunction with other physical parameters such as stable extrusion force. A negative $\Delta$ Tan $\delta$ 1 Hz value can be indicative of a stability improvement due to the addition of pyruvate.

In some embodiments, the gel has a $\Delta$ Tan $\delta$ 1 Hz of about 0.004 or less, about 0.001 or less, about 0 or less, about −0.002 or less, about −0.004 or less, or about −0.006 or less, after heat sterilization. In some embodiments, the gel has a $\Delta$ Tan $\delta$ 1 Hz of about −0.01 or less, about −0.03 or less, or about 0.04 or less, after storage for about 60 days at about 45° C. as compared to a similar gel lacking pyruvate In some embodiments, an HA composition can be injected through a 27 gauge needle at a speed of about 13 mm/min with an extrusion force of about 9 N to about 13 N, about 10 N to about 12 N, or about 11 N, after heat stabilization.

An HA composition may be used to treat a soft tissue condition of an individual. As used herein, the term "treating," includes to reducing any detectable amount or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term treating includes reducing a symptom of a condition characterized by a soft tissue defect, disease, and/or disorder by any detectable amount. In some embodiments, a symptom may be reduced at least about 20%, at least about 30%, at least about 40%, at least about 50%, at least about 60%, at least about 70%, at least about 80%, at least about 90% or at least about 100%. The effectiveness of a hydrogel composition disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A soft tissue condition may include, without limitation, a soft tissue imperfection, defect, disease, and/or disorder, such as a breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, a mesotherapy, Parry-Romberg syndrome, lupus erythematosus profundus, dermal divots, scars, sunken cheeks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas. As used herein, the term "mesotherapy" includes a non-surgical cosmetic treatment technique of the skin involving intra-epidermal, intra-dermal, and/or subcutaneous injection of an agent administered as small multiple droplets into the epidermis, dermo-epidermal junction, and/or the dermis.

The amount of an HA composition used may be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

For example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

In some embodiments, the amount of a hydrogel composition administered is, e.g., about 0.01 g, about 0.05 g, about 0.1 g, about 0.5 g, about 1 g, about 5 g, about 10 g, about 20 g, about 30 g, about 40 g, about 50 g, about 60 g, about 70 g, about 80 g, about 90 g, about 100 g, about 150 g, or about 200 g, about 0.01 g to about 0.1 g, about 0.1 g to about 1 g, about 1 g to about 10 g, about 10 g to about 100 g, or about 50 g to about 200 g, about 0.01 mL, about 0.05 mL, about 0.1 mL, about 0.5 mL, about 1 mL, about 5 mL, about 10 mL, about 20 mL, about 30 mL, about 40 mL, about 50 mL, about 60 mL, about 70 g, about 80 mL, about 90 mL, about 100 mL, about 150 mL, or about 200 mL, about 0.01 mL to about 0.1 mL, about 0.1 mL to about 1 mL, about 1 mL to about 10 mL, about 10 mL to about 100 mL, or about 50 mL to about 200 mL.

Duration of treatment may be determined based on the cosmetic and/or clinical effect desired by the individual and/or physician and the body part or region being treated. For some treatments, administration of an HA composition can effectively treat a soft tissue condition for, e.g., about 6 months, about 7 months, about 8 months, about 9 months, about 10 months, about 11 months, about 12 months, about 13 months, about 14 months, about 15 months, about 18 months, or about 24 months, at least about 6 months, at least about 7 months, at least about 8 months, at least about 9 months, at least about 10 months, at least about 11 months, at least about 12 months, at least about 13 months, at least about 14 months, at least about 15 months, at least about 18 months, or at least about 24 months, about 6 months to about 12 months, about 6 months to about 15 months, about 6 months to about 18 months, about 6 months to about 21 months, about 6 months to about 24 months, about 9 months to about 12 months, about 9 months to about 15 months, about 9 months to about 18 months, about 9 months to about 21 months, about 6 months to about 24 months, about 12 months to about 15 months, about 12 months to about 18 months, about 12 months to about 21 months, about 12 months to about 24 months, about 15 months to about 18 months, about 15 months to about 21 months, about 15 months to about 24 months, about 18 months to about 21 months, about 18 months to about 24 months, or about 21 months to about 24 months.

An HA composition may be administered to a skin region of an individual by injection into a dermal region or a hypodermal region, such as an epidermal-dermal junction region, a papillary region, a reticular region, or any combination thereof.

As used herein, the term "dermal region" refers to the region of skin comprising the epidermal-dermal junction and the dermis including the superficial dermis (papillary region)

and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis includes the layer of skin beneath the epidermis that includes connective tissue and cushions the body from stress and strain. The dermis is tightly connected to the epidermis by a basement membrane. It also harbors many mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It includes loose connective tissue and elastin. The main cell types are fibroblasts, macrophages and adipocytes (the hypodermis contains 50% of body fat). Fat serves as padding and insulation for the body.

Some methods of treating a soft tissue condition of an individual comprise administering an HA composition to a site of a soft tissue condition of the individual to improve or treat the soft tissue condition. In some embodiments a soft tissue condition includes a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

Some methods of treating a skin condition comprise administering an HA composition to an individual suffering from a skin condition to improve or treat the skin condition. Skin dehydration may be treated by administering an HA composition to an individual suffering from skin dehydration to rehydrate the skin, thereby treating skin dehydration. A lack of skin elasticity may be treated by administering an HA composition to an individual suffering from a lack of skin elasticity to increase the elasticity of the skin, thereby treating a lack of skin elasticity. Skin roughness may be treated by administering an HA composition to decrease skin roughness, thereby treating skin roughness. A lack of skin tautness may be treated by administering an HA composition to an individual suffering from a lack of skin tautness to make the skin tauter, thereby treating a lack of skin tautness.

A skin stretch line or mark may be treated by administering an HA composition to an individual suffering from a skin stretch line or mark to reduce or eliminate the skin stretch line or mark, thereby treating a skin stretch line or mark. Skin paleness may be treated by administering and HA composition to an individual suffering from skin paleness to increase skin tone or radiance, thereby treating skin paleness. Skin wrinkles may be treated by administering an HA composition to an individual suffering from skin wrinkles to reduce or eliminate skin wrinkles or makes the skin resistant to skin wrinkles, thereby treating skin wrinkles.

Some methods of treating a skin condition comprise administering an HA composition into a dermal region of the individual, to improve the skin condition. Skin conditions treated by the disclosed compositions include, without limitation, augmentations, reconstructions, diseases, disorders, defects, or imperfections of a body part, region or area. In one aspect, a skin condition treated by the disclosed compositions include, without limitation, a facial augmentation, a facial reconstruction, a facial disease, a facial disorder, a facial defect, or a facial imperfection. In one aspect, a skin condition treated by the disclosed compositions include, without limitation, skin dehydration, a lack of skin elasticity, skin roughness, a lack of skin tautness, a skin stretch line or mark, skin paleness, a dermal divot, a sunken cheek, a thin lip, a retro-orbital defect, a facial fold, or a wrinkle.

EXAMPLES

In the experiments reported herein, the impact on the stability of an HA gel and the ingredients were shown by incorporating sodium pyruvate (i) alone in a gel containing lidocaine, or (ii) with other additives such as acorbic acid, sodium ascorbyl phosphate, vitagen.

Example 1: Incorporation of Sodium Pyruvate to a Gel with Lidocaine and Autoclaving Stability Sodium pyruvate was incorporated into a matrix NaHA gel with lidocaine (with 0.3% w/w lidocaine) with a content of 0.01% w/w to 1% w/w. The gels were autoclaved. Extrusion force (F) was measured with 27 G needle and a speed of 13 mm/min. A Gel is considered as stable during autoclaving if $-2N \leq \Delta F \leq 2N$ with $\Delta F = (F$ gel with additives$) - (F$ NaHA control$)$ and if $\Delta$ Tan $\delta 1$ Hz$\leq 0.1$ with $\Delta$ Tan $\delta 1$ Hz$=($Tan $\delta 1$ Hz gel with additives$)-$ (Tan $\delta 1$ Hz NaHA control)

Rheological properties of the gels are followed as a function of frequency using a controlled stress rheometer according the following method: frequency sweep from 0.05 Hz to 10 Hz with 0.8% controlled strain. G' is elastic modulus. G" is viscous modulus. Tan $\Delta$ shows the ratio of viscous modulus to elastic modulus (it shows the degradation of the gel). Table 1 shows the compositions tested and the $\Delta$ Tan $\delta$ 1 Hz obtained after autoclaving between 120° C. and 130° C. for 5 to 15 minutes. The results in Table 1 show that, at least about for these compositions, addition of pyruvate in the gel preserves the stability of the gel and can improve their stability above 0.25%.

TABLE 1

| % pyruvate | % lidocaine | ΔF | Δ Tan δ 1 Hz |
|---|---|---|---|
| 0.01 | 0.3 | −0.3 | 0.004 |
| 0.05 | 0.3 | −0.6 | 0.001 |
| 0.10 | 0.3 | −0.1 | 0.001 |
| 0.25 | 0.3 | −0.2 | 0.001 |
| 0.50 | 0.3 | −0.5 | −0.007 |
| 1.00 | 0.3 | −0.2 | −0.006 |

Example 2: Thermal Stability of Formulation Example 1

Figure 2:
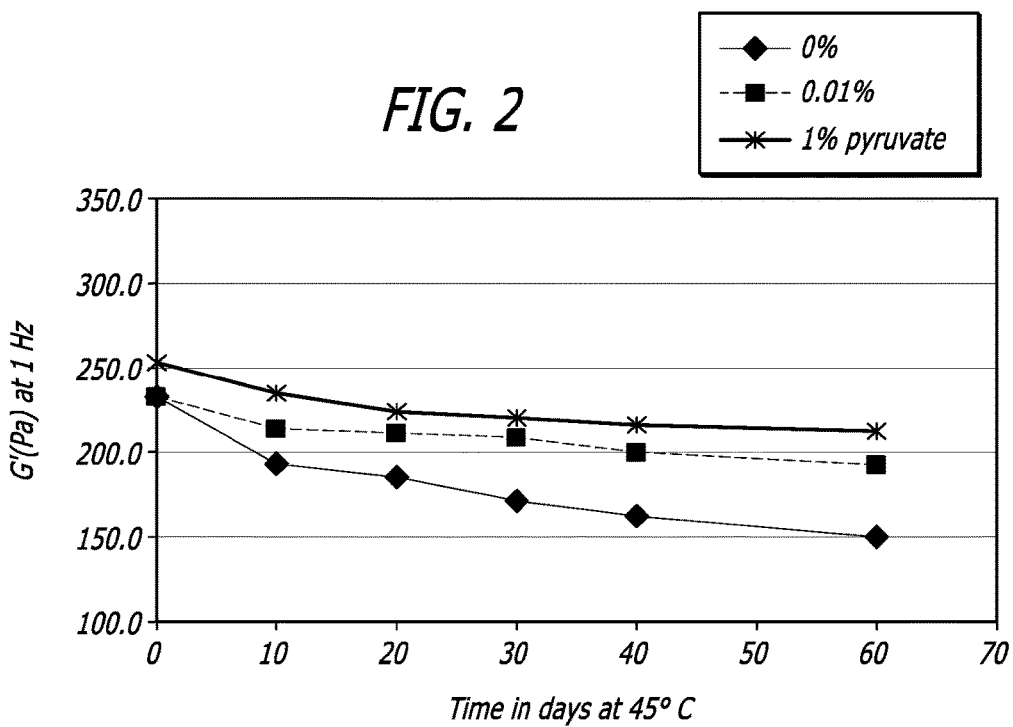
FIG. 2 is a plot of elastic modulus of some compositions of Example 1 as they are stored at 45° C. for 60 days.
Figure 3:
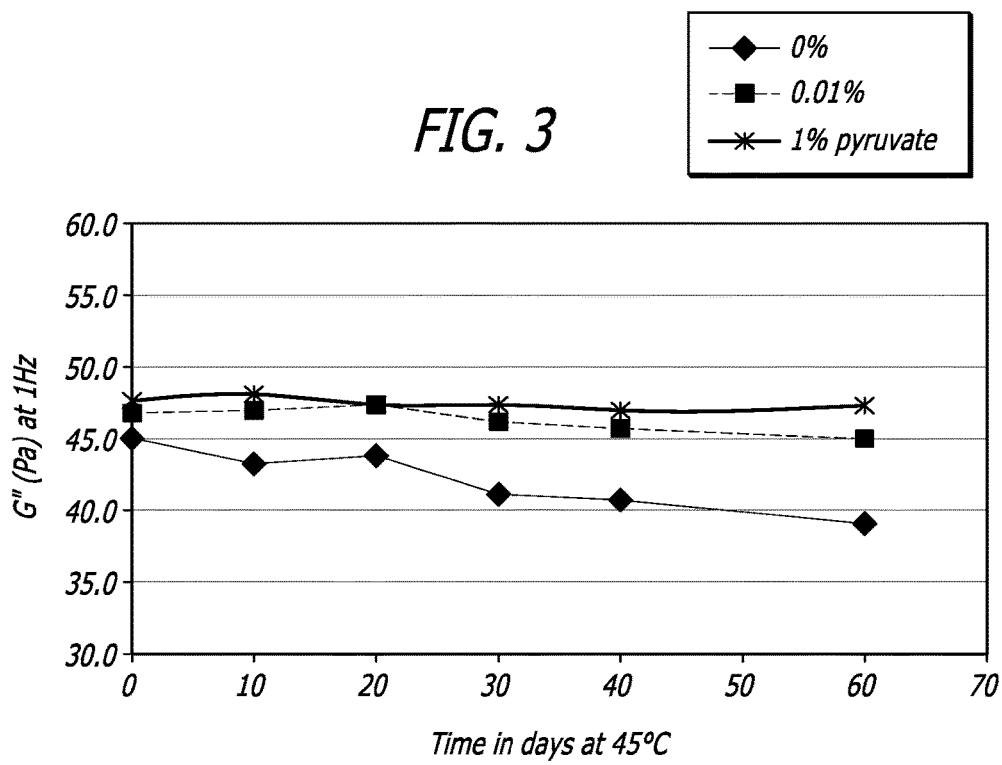
FIG. 3 is a plot of viscous modulus of some compositions of Example 1 as they are stored at 45° C. for 60 days.

The shelf-life at 45° C. during 60 days was tested of the formulations prepared in example 1 and the NaHA matrix with Lidocaine. The pH of the gels were stable in time. Rheological properties were followed for 60 days at 45° C. FIG. 1 is a plot of extrusion force, FIG. 2 is a plot of elastic modulus, and FIG. 3 is a plot of viscous modulus of the control (0% pyruvate), and the HA compositions comprising 0.01% pyruvate and 1% pyruvate and as they were stored at 45° C. for 60 days. Table 2 shows that, for these compositions, the addition of pyruvate in a gel helps to stabilize the gel. The effect on tan L increase during storage at 45° C. is correlated to the pyruvate content, with a stability improvement plateau reached at about 0.25%.

TABLE 2

| % pyruvate | % lidocaine | Δ Tan δ 1 Hz 60 days at 45° C. |
|---|---|---|
| 0.01 | 0.3 | −0.032 |
| 0.05 | 0.3 | −0.036 |
| 0.10 | 0.3 | −0.038 |
| 0.25 | 0.3 | −0.040 |
| 0.25 | 0.3 | −0.040 |
| 1.00 | 0.3 | −0.041 |

Δ Tan δ 1 Hz = (Tan δ 1 Hz gel with additives at 60 days) − (Tan δ 1 Hz NaHA control at 60 days)
Gel stability is improved by pyruvate if Δ Tan δ 1 Hz at 60 days < 0

Example 3: Incorporation of Sodium Pyruvate to a Formulation Containing Vitagen, Lidocaine and Autoclaving Stability Sodium pyruvate was incorporated into a matrix of NaHA gel with Lidocaine (with 0.3% w/w lidocaine) and vitagen with a content of 0.6% w/w. The gels were autoclaved between 120° C. and 130° C. for 5 to 15 minutes. As shown in Table 3, an increase of the stability (pH, extrusion force, tan delta) after autoclaving is observed in compositions containing pyruvate while the composition containing Vitagen without pyruvate is not stable during autoclaving.

TABLE 3

| % pyruvate | % vitagen | % lidocaine | pH | ΔF | Δ Tan δ 1 Hz |
|---|---|---|---|---|---|
| 0 | 0 | 0 | 7.07 | 0 | 0 |
| 0 | 0.6 | 0 | 6.86 | 2.6 | 0.072 |
| 1 | 0.6 | 0 | 7.08 | −0.57 | −0.100 |

ΔF = (F gel with additives) − (F NaHA control)
Δ Tan δ 1 Hz = (Tan δ 1 Hz gel with additives) − (Tan δ 1 Hz NaHA control)
Gel is considered as stable if −2N ≤ Δ F ≤ 2N and Δ Tan δ 1 Hz ≤ 0.1

Example 4: Thermal Stability of Gel Properties Example 3

The shelf-life at 45° C. over 60 days was tested of the formulations prepared in example 1 and the NaHA matrix with Lidocaine. The pH and rheological properties were followed. The addition of pyruvate to the formulation has a significant impact of the stability of a gel with no additive and a gel containing only Vitagen.

Figure 4:
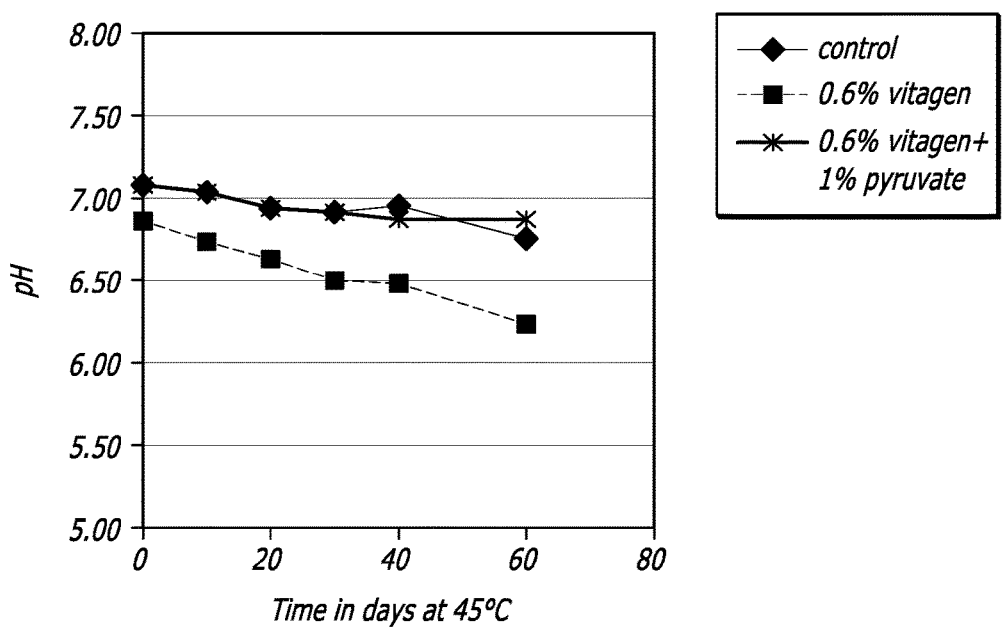
FIG. 4 is a plot of pH of some compositions of Example 1 as they are stored at 45° C. for 60 days.
Figure 5:
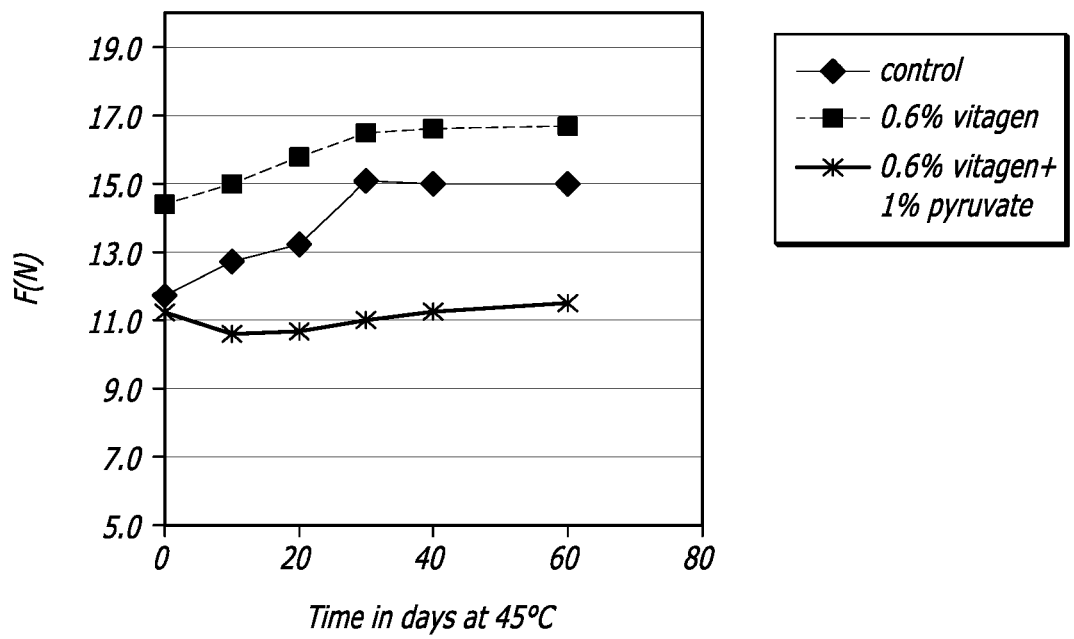
FIG. 5 is a plot of extrusion force of some compositions of Example 1 as they are stored at 45° C. for 60 days.
Figure 6:
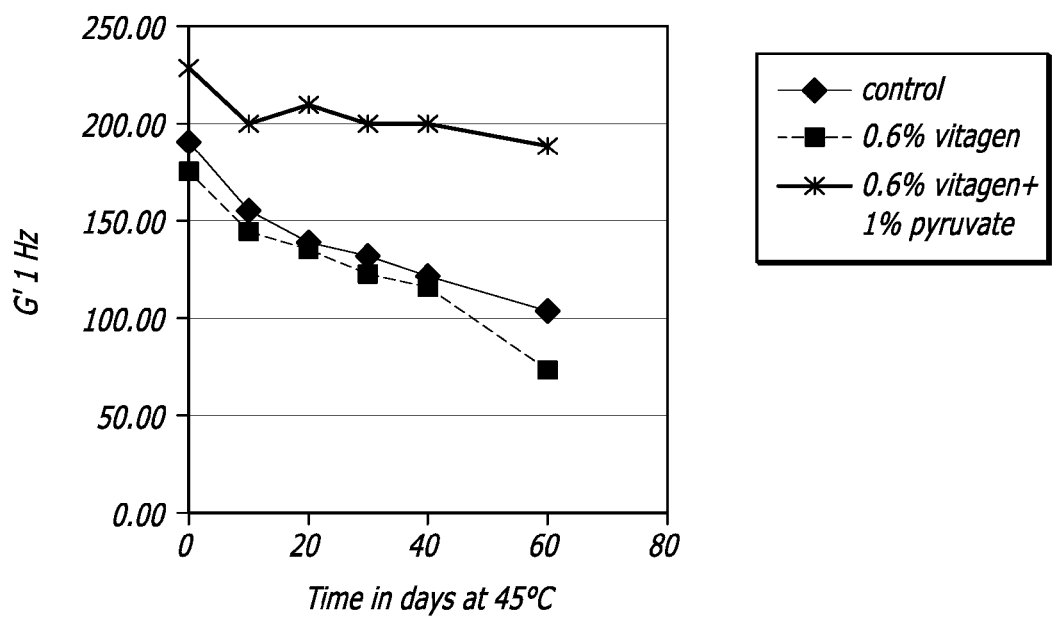
FIG. 6 is a plot of elastic modulus of some compositions of Example 1 as they are stored at 45° C. for 60 days.
Figure 7:
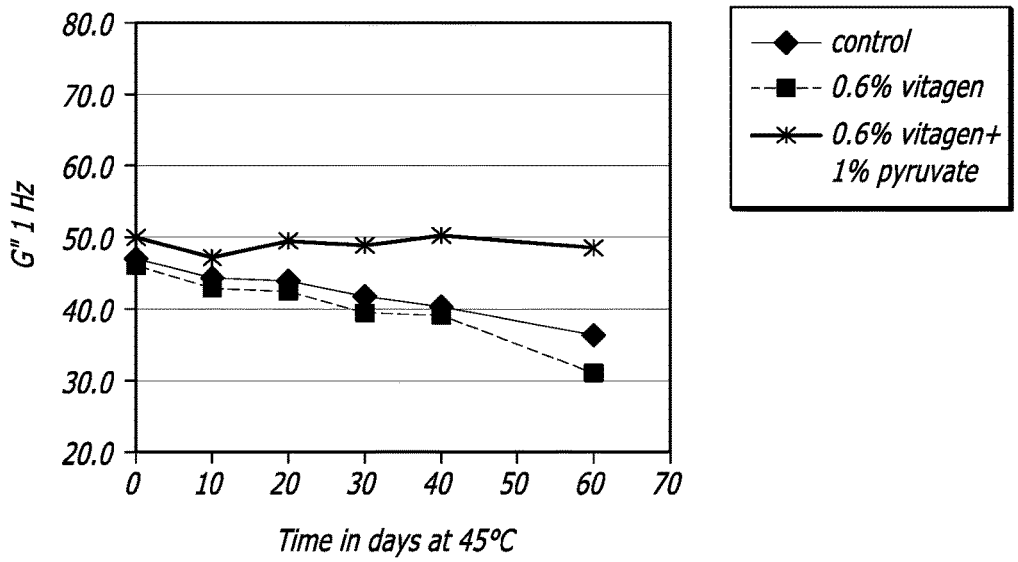
FIG. 7 is a plot of viscous modulus of the compositions of Example 1 as they are stored at 45° C. for 60 days FIG. 8 a plot of tan delta of the compositions of Example 1 as they are stored at 45° C. for 60 days.
Figure 8:
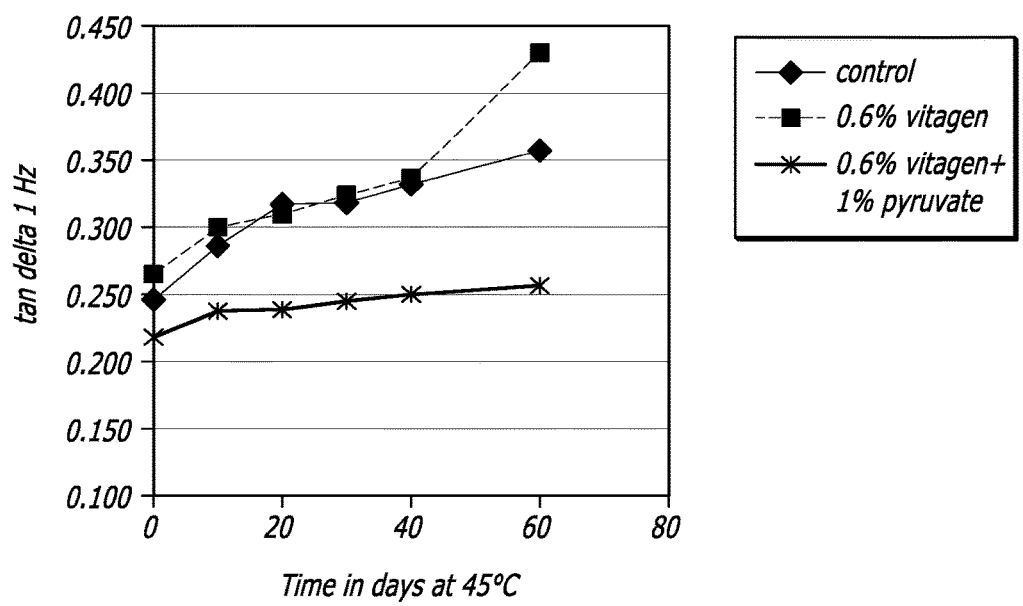

As shown in FIG. 4, the addition of the Vitagen (alone) in the formulation leads to a pH decrease of the gel over time. Addition of pyruvate allows pH to be better maintained. As a result of the improved pH stability, rheological properties are better maintained. (FIGS. 5-8)

Example 5: Thermal Stability of the Additive Vitagen Present in Gel of Example 3

The amount of Vitagen remaining on the autoclaved samples of Example 3 was quantified by HPLC. Table 4 shows that addition of pyruvate to a formulation containing Vitagen contributes to stabilize the additive during thermal stability.

TABLE 4

| % pyruvate | % Vitagen | % lidocaine | % Vitagen lost at 60 days |
|---|---|---|---|
| 0 | 0.6 | 0 | 14% |
| 1 | 0.6 | 0.3 | 1.5% |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least about be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience or any other reason. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A composition comprising:
   a hyaluronic acid, about 0.1% w/w to about 1% w/w of a pyruvate and a vitagen;
   wherein the hyaluronic acid is crosslinked; and
   wherein the composition is a gel that is stable to heat sterilization, wherein the gel has a $\Delta F$ of $-2N \leq \Delta F \leq 2N$ after heat sterilization and a $\Delta$ Tan $\delta 1$ Hz$\leq 0.1$ after heat sterilization, and is suitable for use as a dermal filler.

2. The composition of claim 1, wherein the gel has improved thermal stability as compared to a substantially identical gel lacking pyruvate.

3. The composition of claim 1, wherein the gel has improved thermal stability as compared to a substantially identical gel lacking both vitagen and pyruvate.

4. The composition of claim 1, wherein the vitagen is in amount of about 0.6% w/w.

5. The composition of claim 1, further comprising lidocaine.

6. The composition of claim 5, wherein the lidocaine is present in amount in the range of about 0.05% w/w to about 1% w/w.

7. The composition of claim 1, wherein the pyruvate is present in an amount of 0.1% and the vitagen is present in an amount of 0.6%.

8. The composition of claim 1, wherein the gel has a $\Delta$ Tan $\delta$ 1 Hz of less than about 0.004 after heat sterilization.

9. The composition of claim 1, wherein the gel has a $\Delta$ Tan $\delta$ 1 Hz of less than about 0.03 after storage for 60 days at about 45° C.

10. The composition of claim 1, wherein the hyaluronic acid comprises a combination of a low molecular weight hyaluronic acid fraction and a high molecular weight hyaluronic acid fraction.

11. The composition of claim 10, wherein the high molecular weight hyaluronic acid fraction has mean molecular weight of 1,000,000 Da or greater and the low molecular weight hyaluronic acid fraction has a mean molecular weight of less than 1,000,000 Da.

12. The composition of claim 10, wherein a weight ratio of the high molecular weight hyaluronic acid fraction to the low molecular weight hyaluronic acid fraction is about 20, about 15, about 10, about 5, about 1, about 0.07, about 0.05, about 0.2, or about 0.1.

13. The composition of claim 1, wherein the pyruvate is pyruvic acid.

14. The composition of claim 1, wherein the pyruvate is a sodium salt, a potassium salt, a lithium salt, a magnesium salt, or a calcium salt.

15. A dermal filler composition comprising crosslinked hyaluronic acid and pyruvate in an amount of about 0.1% w/w to about 1% w/w, wherein the composition has a $\Delta F$ of $-2N \leq \Delta F \leq 2N$ after heat sterilization and a $\Delta$ Tan $\delta 1$ Hz$\leq 0.1$ after heat sterilization.

16. The composition of claim 15, wherein the pyruvate is pyruvic acid.

17. The composition of claim 15, wherein the pyruvate is a sodium salt, a potassium salt, a lithium salt, a magnesium salt, or a calcium salt.

18. The composition of claim 15, further comprising lidocaine.

19. The composition of claim 18, wherein the lidocaine is present in amount in the range of about 0.05% w/w to about 1% w/w.

* * * * *